United States Patent [19]

Ogihara et al.

[11] Patent Number: 5,523,439
[45] Date of Patent: Jun. 4, 1996

[54] PROCESS FOR PREPARING SILACYCLOHEXANE COMPOUNDS

[75] Inventors: Tsutomu Ogihara; Takaaki Shimizu; Takeshi Kinsho; Tatsushi Kaneko, all of Niigata-ken, Japan

[73] Assignee: Shin-Etsu Chemical Co., Ltd., Tokyo, Japan

[21] Appl. No.: 511,816

[22] Filed: Aug. 7, 1995

[30] Foreign Application Priority Data

Aug. 8, 1994 [JP] Japan .................. 6-205931

[51] Int. Cl.⁶ .................. C07F 7/08; C07F 7/18
[52] U.S. Cl. .............. 512/406; 204/157.44; 204/157.45; 204/157.74
[58] Field of Search ............ 556/406; 204/157.44, 204/157.45, 157.64, 157.74

[56] References Cited

U.S. PATENT DOCUMENTS 4,973,723  11/1990  Cawthorn et al. ............ 556/406
5,454,977  10/1995  Shimizu et al. .............. 556/406 X Primary Examiner—Paul F. Shaver
Attorney, Agent, or Firm—Lowe, Price, LeBlanc & Becker

[57] ABSTRACT

Processes for selectively preparing silacyclohexane compounds of a trans form from diarylsilacyclohexane compounds of the general formula

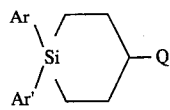

wherein Ar and Ar' independently represent a phenyl group or a tolyl group, and Q represents a group of the type indicated below

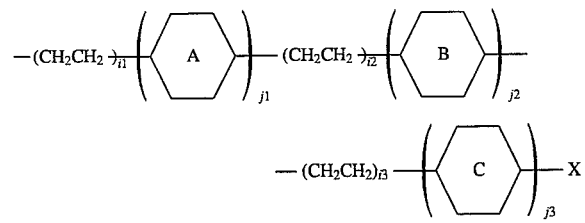

The diarylsilacyclohexanes are converted to dihalosilacyclohexanes and then to hydrohalosilacyclohexanes directly or via dialkoxylation and/or reduction step. The hydrohalosilacyclohexane are finally reacted with organometallic compounds having a group, Q', of the type indicated below

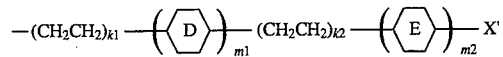

to obtain silacyclohexane compounds of the general formula

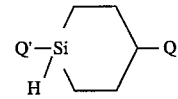

wherein Q' and Q have, respectively, the groups indicated hereinabove.

11 Claims, No Drawings

PROCESS FOR PREPARING SILACYCLOHEXANE COMPOUNDS

BACKGROUND OF THE INVENTION

1. Field of the Invention

This invention relates to a process for preparing silacyclohexane compounds which serve as a liquid crystal.

2. Description of the Prior Art

The liquid crystal display devices make use of optical anisotropy and dielectric anisotropy of liquid crystal substances. Depending on the mode of display, there are a variety of display systems including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid substances used in these liquid crystal devices depend, more or less, on the type of display, it is commonly required that the liquid crystal substances have a wide range of liquid crystal working temperatures and that they be stable against moisture, air, light, heat, electric field and the like. Moreover, the liquid crystal substances should desirably be low in viscosity and should ensure a short address time, a low threshold voltage and a high contrast in a cell.

As the liquid crystal display devices have wider utility in recent years, the characteristic properties required for liquid crystal materials become much severer. In addition, those characteristics which have never been required for conventional liquid crystal substances are now expected such as a lower drive voltage, a wider working temperature range which could satisfy the needs for on-vehicle materials and an improvement in low temperature performance.

Under these circumstances, we developed novel silacyclohexane-based liquid crystal compounds which contain a silicon atom in the molecule so that the characteristic properties for use as a liquid crystal substance are improved. These liquid crystal compounds have been proposed, for example, in co-pending U.S. application Ser. Nos. 08/377,961, filed Jan. 25, 1995 and 08/395,706, filed Feb. 28, 1995 (corresponding to European Patent Application Nos. 95101167.5, filed Jan. 27, 1995 and 951029.8.1, filed Mar. 1, 1995 and Korean Patent Application Nos. 95-1701, filed Jan. 28, 1995 and 95-4084, filed Feb. 28, 1995, respectively). These compounds of a trans form are particularly useful as a liquid crystal compound. The compounds obtained at the stage of preparation thereof are in the form of a mixture of cis and trans isomers, which requires separation of the trans isomer from the mixture.

SUMMARY OF THE INVENTION

It is an object of the invention to provide a process for preparing liquid crystal compounds predominantly in the form of a trans form.

It is another object of the invention to provide processes for the selective preparation of silacyclohexane-based liquid crystal compounds of a trans form.

The above objects can be achieved, according to one embodiment of the invention, by a process for preparing a silacyclohexane compound, which comprises the steps of:

(1) subjecting a diarylsilacyclohexane compound of the following general formula (1)

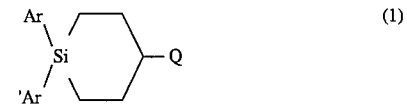

wherein Ar and Ar' independently represent a phenyl group or a tolyl group, and Q represents a group of the following formula (2)

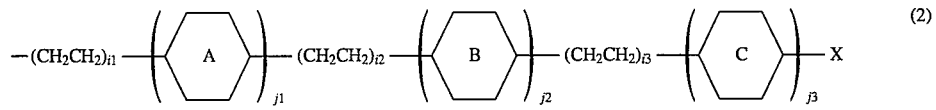

in which

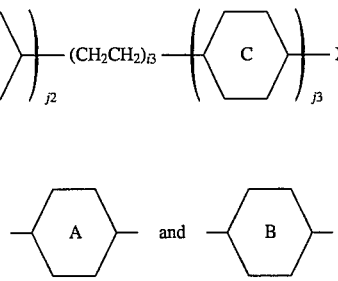

independently represent

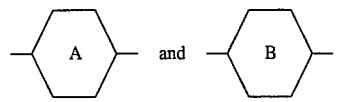

wherein $Y_3$ represents H, F or $CH_3$;

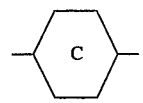

represents

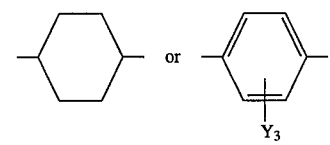

wherein $Y_1$ and $Y_2$ independently represent H, F or Cl; X represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atom, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and i1, i2 and i3 are, respectively, 0 or 1 provided that i1+i2+i3=1 and j1, j2 and j3 are, respectively, a value of 0, 1 or 2 provided that j1+j2+j3=0, 1 or 2, to conversion into a dihalosilacyclohexane compound of the following general formula (3)

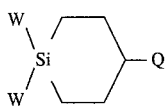
(3)

wherein each W represents a halogen, preferably Cl or Br;

(2) subjecting the compound of the formula (3) to further reaction with an alcohol of the general formula, R'OH, wherein R' represents a linear alkyl group having from 1 to 10 carbon atoms or a branched alkyl group having from 3 to 8 carbon atoms, thereby obtaining a dialkoxysilacyclohexane compound of the following general formula (4)

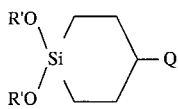
(4)

(3) reducing the compound of the formula (4) to obtain a dihydrosilacyclohexane compound of the following general formula (5)

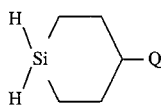
(5)

(4) subjecting the compound of the formula (5) to monohalogenation to obtain a hydrohalosilacyclohexane compound of the following general formula (6)

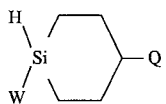
(6)

wherein W represents a halogen, preferably Cl or Br; and (5) subjecting the compound of the formula (6) to reaction with an organometallic reagent of the general formula, Q'—M, wherein (a) Q' represents a group of the following formula (7)

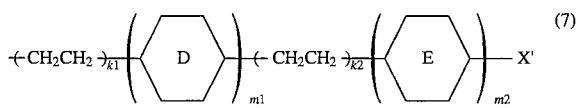
(7)

in which

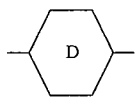

represents

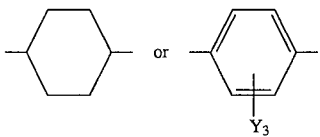

wherein $Y_3$ represents H, F or $CH_3$;

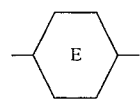

represents

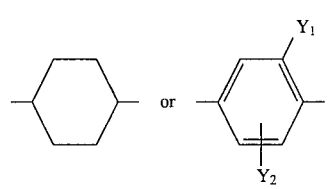

wherein $Y_1$ and $Y_2$ independently represent H, F or Cl; X' represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and k1 and k2 are independently a value of 0 or 1 provided that k1+k2=1, m1 and m2 are independently represent a value of 0, 1 or 2 provided that m1+m2=0, 1 or 2; and (b) M represents MgP or ZnP wherein P represents a halogen, preferably Cl, Br or I, thereby obtaining a silacyclohexane compound of the following general formula (I)

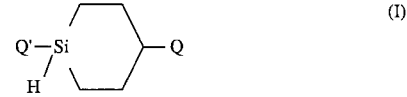
(I)

wherein Q' and Q have, respectively, the same meanings defined above.

According to another embodiment of the invention, there is also provided a process for preparing a silacyclohexane compound of the above-defined general formula (I) in which the step (2) of the process according to the first embodiment is omitted, i.e. the compound of the general formula (3) is reduced to obtain the compound of the general formula (5). More particularly, the process of this embodiment comprises the steps of:

(1) subjecting a diarylsilacyclohexane compound of the following general formula (1)

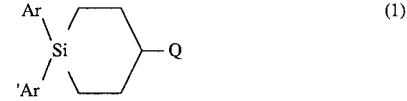
(1)

wherein Ar and Ar' independently represent a phenyl group or a tolyl group, and Q represents a group of the following formula (2)

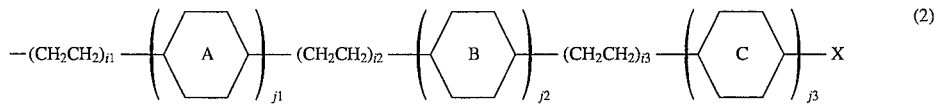
(2)

in which

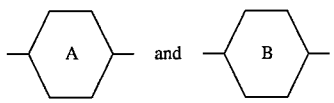

independently represent

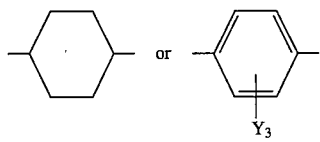

wherein $Y_3$ represents H, F or $CH_3$;

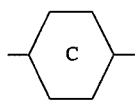

represents

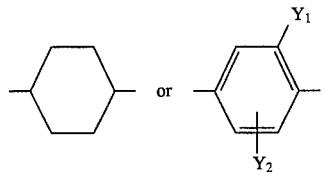

wherein $Y_1$ and $Y_2$ independently represent H, F or Cl;
X represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and i1, i2 and i3 are, respectively, a value of 0 or 1 provided that i1+i2+i3=1 and j1, j2 and j3 are, respectively, a value of 0, 1 or 2 provided that j1+j2+j3=0, 1 or 2, to conversion into a dihalosilacyclohexane compound of the following general formula (3)

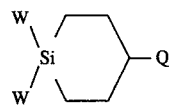

wherein each W represents a halogen, preferably Cl or Br;

(2) reducing the compound of the formula (3) to obtain a dihydrosilacyclohexane compound of the following general formula (5)

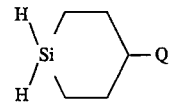

(3) subjecting the compound of the formula (5) to monohalogenation to obtain a hydrohalosilacyclohexane compound of the following general formula (6)

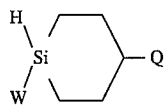

wherein W represents a halogen, preferably Cl or Br; and (4) subjecting the compound of the formula (6) to reaction with an organometallic reagent of the general formula, Q'—M, wherein (a) Q' represents a group of the following formula (7)

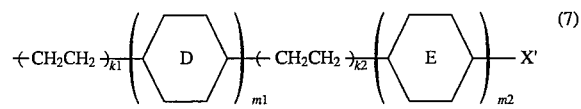

in which

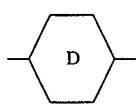

represents

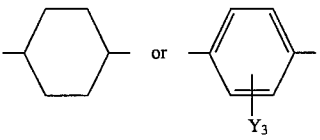

wherein $Y_3$ represents H, F or $CH_3$;

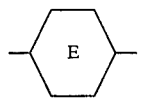

represents

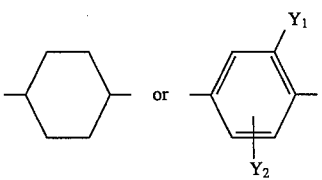

wherein $Y_1$ and $Y_2$ independently represent H, F or Cl;
X' represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and k1 and k2 are independently a value of 0 or 1 provided that k1+k2=1, m1 and m2 are independently represent a value of 0, 1 or 2 provided that m1+m2=0, 1 or 2; and (b) M represents MgP or ZnP wherein P represents a halogen, preferably Cl, Br or I, thereby obtaining a silacyclohexane compound of the following general formula (I)

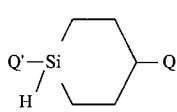 (I)

wherein Q' and Q have, respectively, the same meanings defined above.

According to a further embodiment of the invention, there is provided a process for preparing a silacyclohexane compound of the above-defined general formula (I) in which the steps (2) and (3) of the process according to the first embodiment are omitted, i.e. the compound of the general formula (3) is directly converted to a hydrohalosilacyclohexane compound of the afore-indicated formula (6). More particularly, the process of this embodiment comprises the steps of:

(1) subjecting a diarylsilacyclohexane compound of the following general formula (1)

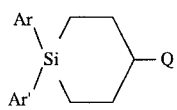 (1)

wherein Ar and Ar' independently represent a phenyl group or a tolyl group, and Q represents a group of the following formula (2)

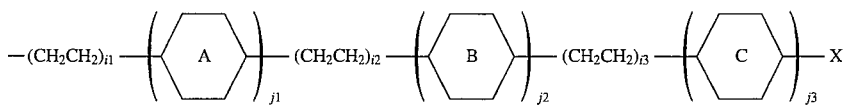 (2)

in which

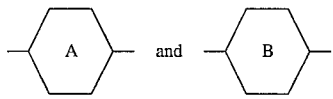

independently represent

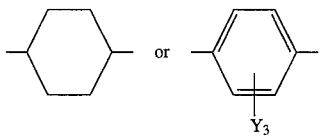

wherein $Y_3$ represents H, F or $CH_3$;

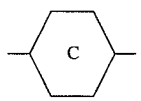

represents

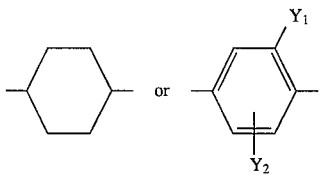

wherein $Y_1$ and $Y_2$ independently represent H, F or Cl;
X represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and i1, i2 and i3 are, respectively, a value of 0 or 1 provided that i1+i2+i3=1 and j1, j2 and j3 are, respectively, a value of 0, 1 or 2 provided that j1+j2+j3=0, 1 or 2, to conversion into a dihalosilacyclohexane compound of the following general formula (3)

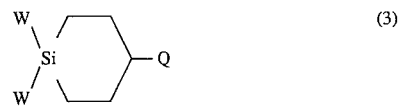 (3)

wherein each W represents a halogen, preferably Cl or Br;

(2) reducing the compound of the formula (3) under conditions sufficient to obtain a hydrohalosilacyclohexane compound of the following general formula (6)

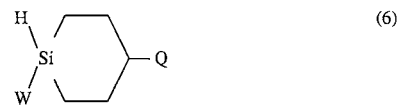 (6)

wherein W has the same meaning as defined above; and (3) subjecting the compound of the formula (6) to reaction with an organometallic reagent of the general formula, Q'—M, wherein (a) Q' represents a group of the following formula (7)

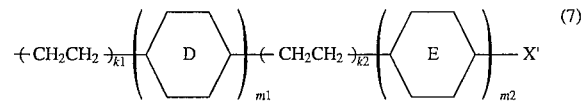 (7)

in which

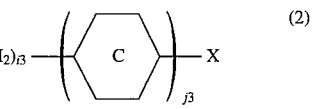

represents

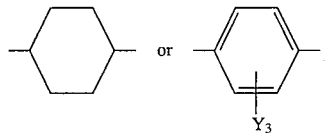

wherein $Y_3$ represents H, F or $CH_3$;

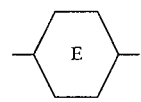

represents

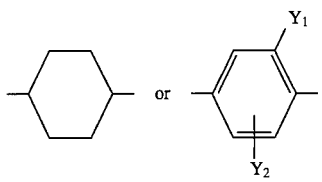

wherein $Y_1$ and $Y_2$ independently represent H, F or Cl; X' represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and k1 and k2 are independently a value of 0 or 1 provided that k1+k2=1, m1 and m2 are independently represent a value of 0, 1 or 2 provided that m1+m2=0, 1 or 2; and (b) M represents MgP or ZnP wherein P represents a halogen, preferably Cl, Br or I, thereby obtaining a silacyclohexane compound of the following general formula (I)

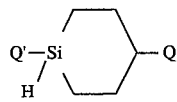

wherein Q' and Q have, respectively, the same meanings defined above.

DETAILED DESCRIPTION OF THE INVENTION

As is known in the art, ordinary liquid crystal compositions are in use in the form of mixtures consisting of as many as 10 to 20 compounds. These compounds contain homologues which have a substantially similar core or skeletal structure only with a difference in folded chain length. With existing hydrocarbon liquid crystal compositions, if the lengths of the folded chains differ from one another, the starting material which is employed at the most upstream stage is prepared to fix with respect to the length of folded chain, from which an intended product is prepared through several tens steps of reactions. In this connection, however, according to the invention, it is possible to prepare silicon-containing liquid crystal compounds whose length and type of folded chain can be arbitrarily determined at a final step of a multistage reaction procedure. For known hydrocarbon liquid crystal compounds, such a determination is not possible. This is possible only for silicon-containing liquid crystal compounds. Especially, in the field of applications of liquid crystal compounds wherein a diversity of compounds having similar structures have to be prepared, such a preparatory procedure as set out hereinabove enables one to reduce the number of reaction steps as a whole, thus leading to a very good economy.

The embodiments of the invention are described. It will be noted that Ar, Ar', P, Q, Q', R, R', T, X, X', $X_1$, $X_2$, $X_3$, $Y_1$–$Y_3$, W, Y, Z, i1–i3, j1–j3, k1, k2, m1, and m2 which have, respectively, been defined in the foregoing formulas have, respectively, the same meanings as defined hereinbefore and may not be sometimes defined again in formulas appearing hereinafter.

The dihalosilacyclohexane used in all the embodiments of the invention is of the following formula (3)

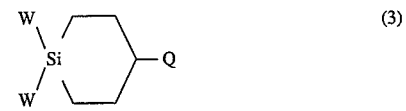

This compound is prepared from a diarylsilacyclohexanone compound through a diarylsilacyclohexane compound by use of an electrophilic reagent EW, in which W represents a halogen, according to a procedure set out in Japanese Patent Application No. 6-78125, filed Mar. 24, 1994 and not yet laid open. This is particularly shown in the following reaction formula (8)

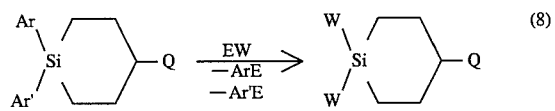

wherein Ar and Ar' independently represent a phenyl group or a tolyl group, and Q represents a group of the general formula (2) defined hereinbefore. In the formula (2), X may represent a group of R or OR along with CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$. In the case, each R represents a linear alkyl group having from 1 to 10 carbon atoms, a branched alkyl group having from 3 to 8 carbon atoms, an alkoxyalkyl group having from 2 to 7 carbon atoms, or an alkenyl group having from 2 to 8 carbon atoms.

Examples of the linear alkyl group having from 1 to 10 carbon represented by R include methyl, ethyl, n-propyl, n-butyl, n-pentyl, n-hexyl, n-heptyl, n-octyl, nonomyl and n-decyl. Examples of the branched alkyl group having 3 to 8 carbon atoms include iso-propyl, 1-methylpropyl, 2-methylpropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl and ethoxypentyl. Examples of the alkenyl group include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl and 7-octenyl.

The electrophilic reagents used for the reaction formula (8) include halogens, hydrogen halides, metal halides, sulfonic derivatives, acid halides, alkyl halides and the like. Preferably, there are mentioned bromine, iodine, chlorine, iodine monochloride, hydrogen chloride, hydrogen bromide, hydrogen iodide, mercury (II) chloride, trimethylsilyl chlorosulfonate, acetyl chloride, acetyl bromide, benzoyl chloride, t-butyl chloride and the like. In order to increase the reaction velocity, Lewis acids such as aluminium chloride, zinc chloride, titanium tetrachloride, boron trifluoride and the like may be added to the reaction system. Alternatively, the reaction system may be irradiated with actinic light such as ultraviolet rays and/or visible rays.

Preferably, this reaction using the electrophilic agent is carried out at a temperature of from 0° to 80° C., more preferably from 10° to 40° C.

The resultant dihalosilacyclohexane compound has two halogen atoms directly bonded to the silicon atom, one of which can be converted to hydrogen atom by using a reducing agent in a stoichiometric amount sufficient for conversion of one halogen atom into a hydrogen atom. This is particularly shown in the following reaction formula (9)

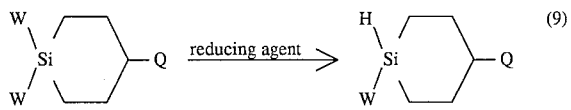

The reducing agents used include, for example, metal hydrides such as sodium hydride, calcium hydride, trialkylsilanes, boranes, dialkylaluminiums and the like, complex hydrides such as lithium aluminium hydride, sodium borohydride, lithium borohydride, potassium borohydride, tributylammonium borohydride and the like, and substituted hydrides thereof such as lithium trialkoxyaluminium hydrides, sodium di(methoxyethoxy)aluminium hydride, lithium triethylborohydride, sodium cyanoborohydride and the like. The reduction reaction is preferably effected at a temperature of from 0° to 100° C. In general, the reduction reaction is carried out in a solvent such as diethyl ether, tetrahydrofuran, dioxane, toluene, xylene, hexane, isooctane or the like.

The resultant hydrohalosilacyclohexane compound is then subjected to carbon-silicon bonding reaction with an organometallic reagent of the formula, Q'—M, wherein Q' and M have, respectively, the same meanings as defined hereinbefore to obtain an intended silacyclohexane compound of the general formula (I)

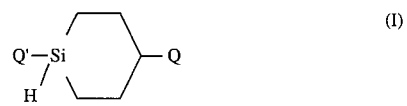

This reaction is shown in the following formula (10)

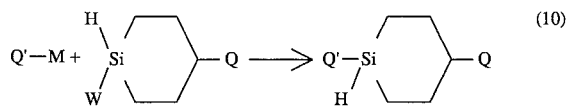

At the time of the above carbon-silicon reaction, a trans isomer useful as a liquid crystal compound is obtained at high selectivity. This reaction is preferably effected at a temperature of from 50° to 150° C. for a time ranging from 0.1 to 5 hours until the reaction is completed.

Alternatively, the dihalosilacyclohexane compound obtained in the formula (8) indicated hereinbefore may be converted into a dihydrosilacyclohexane compound. To this end, one equivalent of the dihalosilacyclohexane compound is reacted with two equivalents of a reducing agent as shown in the reaction formula (11)

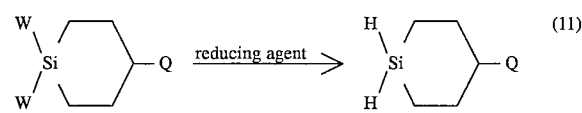

The reducing agents and reaction conditions in this case may be those used in the reaction formula (9), respectively.

The resultant dihydrosilacyclohexane is reacted with a halogenating agent in a stoichiometric amount sufficient for selective monohalogenation thereby obtaining a hydrohalosilacyclohexane according to the following general formula (12)

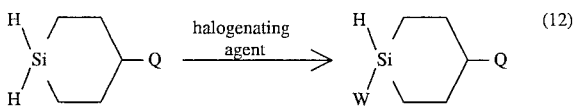

Finally, the intended silacyclohexane compound of the formula (I) is obtained through the carbon-silicon bonding reaction as shown in the aforeindicated formula (10)

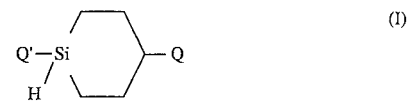

The halogenating agents used in the formula (12) include, for example, halogens such as chlorine, bromine, iodine, iodine chloride and the like, copper chloride+copper iodide, silane halides, metal halides, halides of sulfonic derivatives, alkyl halides and the like ordinarily employed halogenating agents.

The process of this embodiment involves one additional step of the formula (11) on comparison with the embodiment including the steps of the formulas (8) and (9) wherein the hydrohalosilacyclohexane compound is directly formed by the reduction shown in the formula (9). In this connection, however, the hydrohalosilacyclohexane compound may be obtained in a better yield in this embodiment depending on the chemical structure of Q, i.e. the selectivity to the monohalogenation may be adversely influenced depending on the chemical structure of the group, Q. Accordingly, whichever process is selected depends on the chemical structure of Q to be selected.

Still alternatively, the dihalosilacyclohexane compound obtained in the afore-indicated formula (8) may be reacted with an alcohol for conversion into a dialkoxysilacyclohexane compound as shown in the following reaction formula (13)

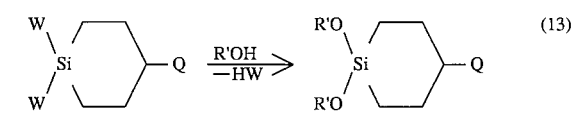

wherein R' has the same meaning as defined before and preferably represents a linear alkyl group having from 1 to 4 carbon atoms or a branched alkyl group having from 3 or 4 carbon atoms. Examples of the linear alkyl group and branched alkyl group are those mentioned with respect to R of the formula (3). Preferable examples of the alcohol represented by the formula, R'OH, include lower alcohols such as methanol, ethanol, n-propyl alcohol, iso-propyl alcohol, n-butyl alcohol and the like. In order to neutralize the resultant hydrogen halide, amines such as triethylamine, urea and the like, or epoxy compounds such as propylene oxide may be added to the reaction system. The reaction with the alcohol is preferably effected at a temperature ranging from 0° to 80° C.

This embodiment include a larger number of steps than those two embodiments set out hereinbefore and is advantageous in that when the dihalosilacyclohexane compound is obtained from the diarylsilacyclohexane compound in the afore-indicated formula (8), a solid catalyst such as aluminum chloride is preferably used. If used, the catalyst can be readily removed when the preparation is conducted through the step of preparing the dialkoxysilacyclohexane compound. On the other hand, if the catalyst is used and left in the step of the afore-indicated formula (10), it may adversely influence the reaction. In this sense, the removal of the catalyst is preferred.

The dialkoxysilacyclohexane compound is then reacted with a reducing agent in an amount of two times by equivalent as great as that of the dialkoxysilacyclohexane compound to obtain a dihydrosilacyclohexane compound according to the following reaction formula (14)

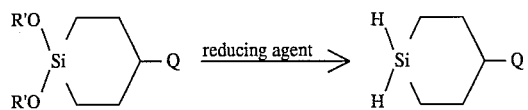

The types of reducing agents and the reduction conditions are similar to those set out hereinbefore with respect to the formula (9).

The thus obtained dihydrosilacyclohexane compound is subjected to monohalogenation with a halogenating agent used in a stoichiometric amount sufficient for the monohalogenation in a manner using a halogenating agent as set out hereinbefore with respect to the afore-indicated formula (12). This is particularly shown in the following reaction formula (15)

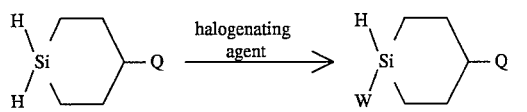

The resultant hydrohalosilacyclohexane compound is reacted with an organometallic compound of the formula, Q'—M, in the same manner as in the foregoing embodiments to obtain an intended silacyclohexane compound (I)

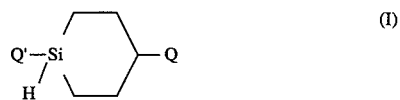

The thus prepared compound may be further purified by a usual manner such as recrystallization, chromatography or the like to an extent necessary for practical applications, thereby obtaining a silacyclohexane-based liquid crystal compound as an intended trans isomer, if necessary.

The present invention is more particularly described by way of examples.

PREPARATORY EXAMPLE 1

Preparation of 4-(trans-4-(3,4-difluorophenyl)cyclohexyl)-1,1-diphenyl-1-silacyclohexane 20.0 g of 3,4-difluoro-1-bromobenzene was dropped in a mixture of 3.0 g of magnesium and 50 ml of tetrahydrofuran (hereinafter referred to simply as THF), followed by refluxing for 3 hours to obtain a Grignard reagent. A solution of 35.0 g of 4-(4,4-diphenyl-4-silacyclohexyl)cyclohexanone in 50 ml of THF was added to the Grignard reagent. After refluxing over 2 hours, the reaction mixture was cooled down to room temperature and then charged into an ammonium chloride aqueous solution, followed by extraction with benzene. 1 g of p-toluenesulfonic acid was added to the benzene solution or phase, after which while refluxing, generated water was separated and removed. At the time when water was stopped distilling off, the mixture was cooled down to room temperature. This mixture was poured into a sodium hydrogencarbonate aqueous solution, followed by washing with brine, drying and concentration by a usual manner. The resultant residue was purified through silica gel chromatography to obtain 4-(4-(3,4-difluorophenyl)-3-cyclohexenyl)- 1,1-diphenyl-1-silacyclohexane. This product was dissolved in 200 ml of ethyl acetate, followed by hydrogenation in the presence of 200 mg of a palladium-carbon catalyst at a pressure of hydrogen of 0.5 MPa. After consumption of the theoretical amount of hydrogen, the catalyst was removed by filtration and the resultant filtrate was concentrated to obtain 42.0 g of 4-(trans-4-( 3,4-difluorophenyl)cyclohexyl)-1,1-diphenyl-1-silacyclohexane. The results of IR analysis are shown below.

IR (liquid film) $\nu_{max}$: 2920, 2850, 1601, 1515, 1425, 1275, 1205, 1115, 980, 940 cm$^{-1}$

EXAMPLE 1

Preparation of trans-(4-(trans-4-(3,4-difluorophenyl)cyclohexyl)- 1-n-pentyl-1-silacyclohexane A solution, in 100 ml of dichloromethane, of 42.0 g of 4-(trans-4-( 3,4-difluorophenyl)cyclohexyl)-1,1-diphenyl-1-silacyclohexane obtained in Preparatory Example 1 was added to 250 ml of a dichloromethane solution of 1.0 mol/liter of iodine monochloride at room temperature, followed by agitation for 1 hour to obtain 4-(trans-4-(3,4-difluorophenyl)cyclohexyl)-1,1-dichloro-1-silacyclohexane. Subsequently, a mixture of 50.0 g of isopropyl alcohol and 300 g of triethylamine was added to the solution at room temperature, followed by agitation under reflux for 1 hour. The resultant solution was concentrated, after which 200 ml of hexane was added thereby permitting secondarily produced hydrochloride to be settled down. The hydrochloride was removed by filtration and the resultant filtrate was concentrated to obtain a mixture of 4-(trans-4-(3,4-difluorophenyl)cyclohexyl)-1,1-diisopropoxy-1-silacyclohexane and acetophenone. This mixture was subjected to distillation under reduced pressure to remove the acetophenone therefrom, and the residue was dissolved in 100 ml of THF and added to a solution of 10.0 g of lithium aluminium hydride in 100 ml of THF. The reaction mixture was agitated under reflux for 1 hour, after which the mixture was poured into 200 ml of 5% hydrochloric acid and extracted with ethyl acetate. The resultant extract was washed with brine, dried and concentrated by a usual manner, followed by purification through silica gel chromatography to obtain 26.2 g of 4-(trans-4-(3,4-difluorophenyl)cyclohexyl)-1-silacyclohexane. The results of IR analysis of the product are shown below.

IR (liquid film) $\nu_{max}$: 2920, 2850, 2140, 1602, 1518, 1278, 1212, 1107, 942, 860, 818 cm$^{-1}$ Thereafter, 25.0 g of 4-(trans-4-(3,4-difluorophenyl)cyclohexyl)-1-silacyclohexane, 23.0 g of copper (II) chloride, and 1.5 g of copper (I) iodide were added to 200 ml of diethyl ether, followed by agitation at room temperature for 8 hours to obtain 4-(trans-4-(3,4-difluorophenyl)cyclohexyl)-1-chloro-1-silacyclohexane. The copper salts were removed from the reaction mixture by filtration, followed by dropping the resultant filtrate in 100 ml of a THF solution of 1 mole/liter of n-pentylmagnesium bromide at room temperature. The reaction mixture was poured into 200 ml of 5% hydrochloric acid and extracted with ethyl acetate. The resultant extract was washed with brine, dried and concentrated by a usual manner, followed by purification through silica gel chromatography to obtain 29.2 g (yield: 90%) of the intended product. The product exhibited nematic liquid crystal properties at a temperature ranging from 14.3° to 71.6° C. and was found to be very useful as a liquid crystal substance. The results of IR analysis are shown below.

IR (liquid film) $\nu_{max}$: 2923, 2845, 2092, 1608, 1520, 1296, 1213, 1113, 891, 825, 808 cm$^{-1}$

EXAMPLE 2

Preparation of trans-(4-(trans-4-(3,4-difluorophenyl)cyclohexyl)- 1-n-propyl-1-silacyclohexane The general procedure of Example 1 was repeated except that a THF solution of n-propylmagnesium bromide was used in place of the THF solution of n-pentylmagnesium bromide, thereby obtaining the captioned product in a similar yield. The product exhibited nematic liquid crystal properties at a temperature between 20.3° and 79.3° C. and was found to be very useful as a liquid crystal substance. The results of IR analysis are shown below.

IR (liquid film) $v_{max}$: 2924, 2854, 2100, 1606, 1518, 1279, 987, 887, 843, 818 cm$^{-1}$ As will be apparent from Examples 1 and 2, the change of only one step permitted liquid crystal compounds to be prepared as having lengths of alkyl groups which differed from each other. The preparation of liquid crystal compounds having different lengths of alkyl groups by changing only one step will not be possible for known, silicon-free liquid crystal compounds.

PREPARATORY EXAMPLE 2

Preparation of 4-(4,4-diphenyl-silacyclohexyl)-4'-fluorobiphenyl

A solution of 25.1 g 4-bromo-4'-fluorobiphenyl in 100 ml of THF was dropped in a mixture of 3.0 g of magnesium and 50 ml of THF, followed by refluxing for 3 hours to obtain a Grignard reagent. A solution of 25.0 g of 1,1-diphenyl-1-silacyclohexanone in 50 ml of THF was added to the Grignard reagent. After refluxing over 2 hours, the reaction mixture was cooled down to room temperature and then charged into an ammonium chloride aqueous solution, followed by extraction with benzene. 1 g of p-toluenesulfonic acid was added to the benzene solution, after which while refluxing, generated water was separated and removed. At the time when water was stopped distilling off, the mixture was cooled down to room temperature. This mixture was poured into a sodium hydrogencarbonate aqueous solution, followed by washing with brine, drying and concentration by a usual manner. The resultant residue was purified through silica gel chromatography to obtain 4-(4,4-diphenyl- 4-silacyclohexenyl)-4'-fluorobiphenyl. This product was dissolved in 200 ml of ethyl acetate, followed by hydrogenation in the presence of 200 mg of a palladium-carbon catalyst at a pressure of hydrogen of 0.5 MPa. After consumption of the theoretical amount of hydrogen, the catalyst was removed by filtration and the resultant filtrate was concentrated to obtain 41.5 g of 4-(4,4-diphenyl-4-silacyclohexyl)-4'-fluorobiphenyl.

EXAMPLE 3

Preparation of trans-4-(4-n-propyl-4-silacyclohexyl)-4'-fluorobiphenyl

A solution, in 100 ml of dichloromethane, of 41.0 g of 4-(4,4-diphenyl- 4-silacyclohexyl)-4'-fluorobiphenyl obtained in Preparatory Example 2 was added to 250 ml of a dichloromethane solution of 1.0 mol/liter of iodine monochloride at room temperature, followed by agitation for 1 hour to obtain 4-(4,4-dichloro- 4-silacyclohexyl)-4'-fluorobiphenyl. The reaction solution was concentrated and the resultant residue was dissolved in 100 ml of THF, which was then added to 100 ml of a THF solution of 10.0 g of lithium aluminium hydride. The reaction mixture was agitated under reflux for 1 hour and then poured into 200 ml of 5% hydrochloric acid, followed by extraction with ethyl acetate. The resultant extract was washed with brine, dried and concentrated by a usual manner, followed by purification through silica gel chromatography to obtain 23.6 g of 4-(4-silacyclohexyl)-4'-fluorobiphenyl.

Subsequently, 23.0 g of 4-(4-silacyclohexyl)-4'-fluorobiphenyl, 23.0 g of copper (II) chloride, and 1.5 g of copper (I) iodide were added to 200 ml of diethyl ether, followed by agitation at room temperature for 8 hours to obtain 4-(4-chloro-4-silacyclohexyl)-4'-fluorobiphenyl. The copper salts were removed from the reaction mixture by filtration, followed by dropping the resultant filtrate in 100 ml of a THF solution of 1 mole/liter of n-propylmagnesium bromide at room temperature. The reaction mixture was poured into 200 ml of 5% hydrochloric acid and extracted with ethyl acetate. The resultant extract was washed with brine, dried and concentrated by a usual manner, followed by purification through silica gel chromatography to obtain 25.5 g (yield: 96%) of the intended product. The product exhibited nematic liquid crystal properties at a temperature ranging from 80.2° to 119.3° C. and was found to be very useful as a liquid crystal substance. The results of IR analysis of the product are shown below.

IR (liquid film) $v_{max}$: 2854, 2198, 2087, 1604, 1497, 1238, 987, 889, 816 cm$^{-1}$

EXAMPLE 4

Preparation of trans-4-(4-n-pentyl-4-silacyclohexyl)-4'-fluorobiphenyl

The general procedure of Example 3 was repeated except that a THF solution of n-pentylamgnesium bromide was used in place of the THF solution of n-propylmagnesium bromide, thereby obtaining the captioned product in a similar yield. The product exhibited nematic liquid crystal properties at a temperature between 71° and 118° C. and was found to be very useful as a liquid crystal substance. The results of IR analysis are shown below.

IR (liquid film) $v_{max}$: 2916, 2852, 2096, 1495, 1238, 982, 883, 835, 810 cm$^{-1}$ As will be apparent from Examples 3 and 4, the change of only one step permitted liquid crystal compounds to be prepared as having lengths of alkyl groups which differed from each other. The preparation of liquid crystal compounds having different lengths of alkyl groups by changing only one step will not be possible for known, silicon-free liquid crystal compounds. Accordingly, with silicon-containing liquid crystal compounds, it is possible to reduce the number of preparation steps to a significant extent, with good economy.

PREPARATORY EXAMPLE 3

Preparation of 4-n-pentyl-1,1-diphenyl-1-silacyclohexane 12.0 g of potassium t-butoxide was added to a mixture of 41.0 g of n-pentyltriphenylphosphonium bromide and 200 ml of THF, thereby preparing a ylide solution which was orange in color. A solution of 28.0 g of 4,4-diphenyl-4-silacyclohexyl carbaldehyde in 50 ml of THF was added to the ylide solution. After agitation at room temperature for 2 hours, the reaction mixture was poured into iced water and extracted with ethyl acetate. The resultant extract was washed with brine, dried and concentrated by a usual manner, followed by addition of hexane to the resultant residue. The resulting crystals of triphenylphosphine oxide were removed by filtration and the filtrate was concentrated. The resultant residue was purified through silica gel chromatography to obtain 4-(n-pentylidene)-1,1-diphenyl-1-silacyclohexane. This product was dissolved in 200 ml of ethyl acetate, followed by hydrogenation in the presence of 200 mg of a platinum oxide catalyst at a pressure of hydrogen of 0.1 MPa. After consumption of the theoretical amount of hydrogen, the catalyst was removed by filtration and the resultant filtrate was concentrated to obtain 31.5 g of 4-n-pentyl-1-diphenyl-1-silacyclohexane.

EXAMPLE 5

Preparation of trans-1-(trans-2-((3,4-difluorophenyl)cyclohexyl)ethyl)- 4-n-pentyl-1-silacyclohexane 14.6 g of acetyl chloride was added to a solution, in 200 ml of dichloromethane, of 30.0 g of 4-n-pentyl-1,1-diphenyl-1-silacyclohexane obtained in Preparatory Example 3 and 24.8 g of aluminium chloride at room temperature, followed by agitation for 1 hour to obtain a mixture of 4-n-pentyl- 1,1-dichloro-1-silacyclohexane and acetophenone. The reaction mixture was concentrated, after which the acetophenone was distilled off under reduced pressure. The residue was dissolved in 100 ml of THF, to which a solution of 10.0 g of lithium aluminium hydride in 100 ml of THF was added. The reaction mixture was agitated under reflux for 1 hour, followed by pouring into 200 ml of 5% hydrochloric acid and extraction with ethyl acetate. The resultant extract was washed with brine, dried and concentrated by a usual manner, followed by purification through silica gel chromatography to obtain 15.0 g of 4-n-pentyl-1-silacyclohexane.

Thereafter, 15.0g of 4-n-pentyl-1-silacyclohexane, 24.2 g of copper (II) chloride, and 1.6 g of copper (I) iodide were added to 200 ml of diethyl ether, followed by agitation at room temperature for 8 hours to obtain 4-n-pentyl- 1-chloro-1-silacyclohexane. The copper salts were removed from the reaction mixture by filtration, after which the resultant filtrate was dropped in 100 ml of a THF solution of 1 mole/liter of trans-2-((3,4-difluorophenyl)cyclohexyl)ethylmagnesium bromide at room temperature. The reaction mixture was poured into 200 ml of 5% hydrochloric acid and extracted with ethyl acetate. The resultant extract was washed with brine, dried and concentrated by a usual manner, followed by purification through silica gel chromatography to obtain 32.1 g of the intended product. The product exhibited nematic liquid crystal properties at a temperature ranging from 14.7° to 28.9° C. The results of IR analysis are shown below.

IR (liquid film) $v_{max}$: 2920, 2850, 2098, 1608, 1518, 1286, 887, 862, 816 $cm^{-1}$

EXAMPLE 6

Preparation of trans-1-(trans-2-((4-fluorophenyl)cyclohexyl)ethyl)- 4-n-propyl-1-silacyclohexane The general procedure of Example 5 was repeated except that a THF solution of trans-2-((4-fluorophenyl)cyclohexyl)ethylmagnesium bromide was used in place of the THF solution of trans-2-((3,4-difluorophenyl)cyclohexyl)ethylmagnesium bromide, thereby obtaining the intended compound.

Thus, the change of only one step enabled one to prepare liquid crystal compounds whose polar groups differed from each other. With known, silicon-free liquid crystal compounds, it was not possible to prepare liquid crystal compounds whose polar groups differed in type by changing only one step. For the preparation of silicon-containing liquid crystal compounds, the number of preparation steps could be reduced significantly with good economy.

PREPARATORY EXAMPLE 4

Preparation of 4-(2-fluorophenyl)ethyl)-1,1-diphenyl-1-silacyclohexane 12.0 g of potassium t-butoxide was added to a mixture of 45.0 g of p-fluorobenzyltriphenylphosphonium bromide and 200 ml of THF, thereby preparing a ylide solution which was orange in color. A solution of 28.0 g of 4,4-diphenyl-4-silacyclohexyl carbaldehyde in 50 ml of THF was added to the ylide solution. After agitation at room temperature for 2 hours, the reaction mixture was poured into iced water and extracted with ethyl acetate. The resultant extract was washed with brine, dried and concentrated by a usual manner, followed by addition of hexane to the resultant residue. The resulting crystals of triphenylphosphine oxide were removed by filtration and the filtrate was concentrated. The resultant residue was purified through silica gel chromatography to obtain 4-(2-(p-fluorophenyl)ethenyl)-1,1-diphenyl-1-silacyclohexane. This product was dissolved in 200 ml of ethyl acetate, followed by hydrogenation in the presence of 200 mg of a platinum oxide catalyst at a pressure of hydrogen of 0.1 MPa. After consumption of the theoretical amount of hydrogen, the catalyst was removed by filtration and the resultant filtrate was concentrated to obtain 36.5 g of 4-(2-(p-fluorophenyl)ethyl)-1,1-diphenyl-1-silacyclohexane.

EXAMPLE 7

Preparation of trans-4-(trans-4-(2-(4-fluorophenyl)ethyl)-1-silacyclohexyl)- 1-n-propylcyclohexane 15.1 g of acetyl chloride was added to a solution, in 200 ml of dichloromethane, of 36.0 g of 4-(2-fluorophenyl)ethyl)-1,1-diphenyl-1-silacyclohexane obtained in Preparatory Example 4 and 25.6 g of aluminium chloride at room temperature, followed by agitation for 1 hour to obtain a mixture of 4-(2-(p-fluorophenyl)ethyl)-1,1-dichloro-1-silacyclohexane and acetophenone. A mixture of 40 g of ethanol and 60 g of triethylamine was added to the solution at room temperature. The resultant reaction mixture was concentrated, after which 200 ml of hexane was added to permit secondarily produced triethylamine hydrochloride to be precipitated. This precipitate was removed by filtration and the resultant filtrate was concentrated, followed by removal of the acetophenone by distillation under reduced pressure to obtain 28.5 g of 4-(2-(p-fluorophenyl)ethyl)-1,1-diethoxy-1-silacyclohexane. This product was dissolved in 100 ml of THF and added to a solution of 10.0 g of lithium aluminium hydride in 100 ml of THF. The reaction mixture was agitated under reflux for 1 hour and then poured into 200 ml of 5% hydrochloric acid, followed by extraction with ethyl acetate. The resultant extract was washed with brine, dried and concentrated, followed by purification through silica gel chromatography to obtain 20.1 g of 4-(2-(p-fluorophenyl)ethyl)-1-silacyclohexane. Thereafter, 20.0 g of 4-(2-(p-fluorophenyl)ethyl)-1-silacyclohexane, 24.2 g of copper (II) chloride, and 1.6 g of copper (I) iodide were added to 200 ml of diethyl ether, followed by agitation at room temperature for 8 hours to obtain 4-(2-(p-fluorophenyl)ethyl)-1-chloro-1-silacyclohexane. The copper salts were removed from the reaction mixture by filtration, after which the resultant filtrate was dropped in 100 ml of a THF solution of 1 mole/liter of 4-n-propylcyclohexylmagnesium bromide at room temperature. The reaction mixture was poured into 200 ml of 5% hydrochloric acid and extracted with ethyl acetate. The resultant extract was washed with brine, dried and concentrated by a usual manner, followed by purification through silica gel chromatography to obtain 21.2 g (68%) of the intended product. The product exhibited nematic liquid crystal properties at a temperature between 40° and 56.7° C. The results of IR analysis are shown below.

IR (KBr, disc) $v_{max}$: 2916, 2841, 2089, 1510, 1223, 891, 820 cm$^{-1}$

EXAMPLE 8

Preparation of trans-4-(trans-4-(2-(4-fluorophenyl)ethyl)-1-silacyclohexyl)-1-n-pentylcyclohexane The general procedure of Example 7 was repeated except that a THF solution of 4-n-pentylcyclohexylmagnesium bromide was used in place of the THF solution of 4-n-propylcyclohexylmagnesium bromide, thereby obtaining the captioned compound. The results of IR analysis and measurement of transition temperatures are shown below.

IR (liquid film) $v_{max}$: 2916, 2845, 2094, 1510, 1223, 887, 823 cm$^{-1}$

Transition temperatures: C21N67I (i.e. C-N transition temperature of 21° C. and N-I transition temperature of 67° C.)

PREPARATORY EXAMPLE 5

Preparation of 4-(p-fluorophenyl)-1,1-diphenyl-1-silacyclohexane 16.5 g of p-fluorobromobenzene was dropped in a mixture of 2.6 g of magnesium and 50 ml of THF, followed by refluxing for 3 hours to obtain a Grignard reagent. A solution of 26.0 g of 4,4-diphenyl-4-silacyclohexanone in 50 ml of THF was added to the Grignard reagent. After refluxing for 2 hours, the reaction mixture was cooled down to room temperature and poured into an ammonium chloride aqueous solution, followed by extraction with benzene. 1 g of p-toluenesulfonic acid was added to the benzene solution. While refluxing, generated water was separated and removed. At the time when the generation of water was stopped, the reaction mixture was cooled down to room temperature. Subsequently, the reaction mixture was charged into a sodium hydrogencarbonate aqueous solution, washed with brine, dried and concentrated by a usual manner. The resultant residue was purified through silica gel chromatography to obtain 33.0 g of 4-(p-fluorophenyl)-1,1-diphenyl-1-sila-3-cyclohexene. This product was dissolved in 200 ml of ethanol and hydrogenated in the presence of 200 mg of a palladium-carbon catalyst under a hydrogen pressure of 0.5 MPa. After consumption of the theoretical amount of hydrogen, the catalyst was removed by filtration and the resultant filtrate was concentrated to obtain 33.1 g of 4-(p-fluorophenyl)-1,1-diphenyl-1-silacyclohexane. The results of IR analysis are shown below.

IR (KBr, disc) $v_{max}$: 2915, 2850, 1601, 1422, 1215, 1108, 975, 875, 825 cm$^{-1}$

EXAMPLE 9

Preparation of trans-4-(p-fluorophenyl)-1-n-heptyl-1-silacyclohexane 15.3 g of acetyl chloride was added to a solution, in 200 ml of dichloromethane, of 30.0 g of 4-(p-fluorophenyl)-1,1-diphenyl-1-silacyclohexane obtained in Preparatory Example 5 and 25.4 g of aluminium chloride at room temperature, followed by agitation for 1 hour. The reaction mixture was subjected to distillation under reduced pressure to obtain 21.0 g of 4-(p-fluorophenyl)-1,1-dichloro-1-silacyclohexane. This product was dissolved in 100 ml of THF and added to a solution of 10.0 g of lithium aluminium hydride in 100 ml of THF. The reaction mixture was agitated under reflux for 30 minutes, after which the mixture was poured into 200 ml of 5% hydrochloric acid and extracted with ethyl acetate. The ethyl acetate solution or extract was washed with brine, dried and concentrated by a usual manner, followed by purification through silica gel chromatography to obtain 14.8 g of 4-(p-fluorophenyl)-1-silacyclohexane. The results of IR analysis are shown below.

IR (liquid film) $v_{max}$: 2920, 2850, 2140, 1600, 1508, 1222, 1157, 941, 881, 862, 829 cm$^{-1}$ Subsequently, 11.8 g of bromine was added to a solution of 14.0 g of 4-(p-fluorophenyl)-1-silacyclohexane in 100 ml of dichloromethane to obtain 4-(p-fluorophenyl)-1-bromo-1-silacyclohexane. The reaction solution was concentrated and the resultant residue was dissolved in 50 ml of diethyl ether, followed by dropping in 100 ml of a THF solution of 1 mole/liter of n-heptylmagnesium bromide at room temperature. The reaction mixture was poured into 200 ml of 5% hydrochloric acid and extracted with ethyl acetate. The resultant ethyl acetate solution was washed with brine, dried and concentrated, followed by purification through silica gel chromatography to obtain 19.0 g (yield: 90%) of the intended product. The results of IR and NMR analyses are shown below.

IR (liquid film) $v_{max}$: 2920, 2100, 1510, 1458, 1408, 1228, 985, 887, 820 cm$^{-1}$ $^{13}$C-NMR (67.5 MHz, CDCl$_3$): 10.56 (s), 12.13 (s), 14.11 (s), 22.74 (s), 24.44 (s), 29.08 (s), 31.85 (s), 83.19 (s), 33.45 (s), 46.92 (s), 114.90 (d), 127.89 (d), 144.81 (d), 161.09 (d) ppm

EXAMPLE 10

Preparation of trans-4-(p-fluorophenyl)-1-n-pentyl-1-silacyclohexane

The general procedure of Example 9 was repeated except that a THF solution of 4-n-pentylmagnesium bromide was used was used in place of the THF solution of n-heptylmagnesium bromide, thereby obtaining the captioned compound.

EXAMPLE 11

Preparation of 4-(trans-4-(trans-4-n-propylcyclohexyl)-4-silacyclohexyl)-1-fluorobenzene In the same manner as in Example 9, 21.0 g of 4-(p-fluorophenyl)-1,1-dichloro-1-silacyclohexane was obtained from 4-(p-fluorophenyl)-1,1-diphenyl-1-silacyclohexane obtained in Preparatory Example 5. This product was dissolved in 100 ml of THF and added to a solution of 0.8 g of lithium aluminium hydride in 100 ml of THF at 0° C. The reaction mixture was agitated as it is for 30 minutes, after which the reducing agent was removed by filtration. The resultant filtrate was concentrated to obtain 4-(p-fluorophenyl)-1-chloro-1-silacyclohexane. The thus obtained product was dissolved in 50 ml of THF, followed by dropping in 100 ml of a THF solution of 1 mole/liter of 4-n-propylcyclohexylmagnesium bromide at room temperatures. The reaction mixture was poured into 200 ml of 5% hydrochloric acid and extracted with ethyl acetate. The ethyl acetate solution was washed with brine, dried and concentrated, followed by purification through silica gel chromatography to obtain 20.0 g of the intended product. This product exhibited nematic liquid crystal properties at a temperature between 56.2° C. and 110.9° C. and was found to be very useful as a liquid crystal substance. The results of IR analysis are shown below.

IR (KBr, disc) $v_{max}$: 2914, 2843, 2102, 1605, 1508, 1225, 985, 887, 879, 812 cm$^{-1}$

EXAMPLE 12

Preparation of 4-(trans-4-(trans-4-n-butylcyclohexyl)-4-silacyclohexyl)-1-fluorobenzene The general procedure of Example 11 was repeated except that a THF solution of 4-n-butylcyclohexylmagnesium bromide was used in place of the THF solution of 4-n-propylcyclohexylmagnesium bromide, thereby obtaining the captioned compound. The compound exhibited nematic liquid crystal properties at a temperature between 40.1° C. and 106.7° C. and was found to be very useful as a liquid crystal substance. The results of IR analysis are shown below.

IR (liquid film) $v_{max}$: 2924, 2919, 2846, 2102, 1604, 1508, 1225, 985, 812 cm$^{-1}$

EXAMPLE 13

Preparation of 4-(trans-(2-(4-(trans-4-n-propylcyclohexyl)ethyl)-4-silacyclohexyl)-1-fluorobenzene In the same manner as in Example 9, 21.0 g of 4-(p-fluorophenyl)-1,1-dichloro-1-silacyclohexane was obtained from 4-(p-fluorophenyl)-1,1-diphenyl-1-silacyclohexane obtained in Preparatory Example 5. A mixture of 50.0 g of methanol and 30 g of triethylamine was added to the solution obtained above, followed by agitation under reflux for 1 hour. The resultant solution was concentrated, to which 200 ml of hexane was added thereby permitting secondarily produced hydrochloride to be precipitated. The precipitate was removed by filtration and the resulting filtrate was concentrated to obtain a mixture of 4-(p-fluorophenyl)-1,1-dimethoxy-1-silacyclohexane and acetophenone. The mixture was subjected to distillation under reduced pressure to remove the acetophenone therefrom. The resultant residue was dissolved in 100 ml of THF and added to a solution of 10.0 g of lithium aluminium hydride in 100 ml of THF. The reaction mixture was agitated under reflux for 1 hour, which was poured into 200 ml of 5% hydrochloric acid and extracted with ethyl acetate. The ethyl acetate solution was washed with brine, dried and concentrated by a usual manner, followed by purification through silica gel chromatography to obtain 14.7 g of 4-(p-fluorophenyl)-1-silacyclohexane. Subsequently, 14.0 g of 4-(p-fluorophenyl)-1-silacyclohexane was added to 100 ml of toluene, into which chlorine gas was blown to obtain 4-(p-fluorophenyl)-1-chloro-1-silacyclohexane. This solution was dropped in 100 ml of a THF solution of 1 mole/liter of trans-2-(4-n-propylcyclohexyl)ethylmagnesium bromide at room temperature. The reaction mixture was charged into 200 ml of 5% hydrochloric acid and extracted with ethyl acetate. The ethyl acetate solution was washed with brine, dried and concentrated, followed by purification through silica gel chromatography to obtain 20.8 g of the intended product. The thus obtained product exhibited nematic liquid crystal properties at a temperature between 49.1° C. and 62.9° C. and was found to be very useful as a liquid crystal substance.

IR (KBr, disc) $v_{max}$: 2908, 2848, 2096, 1603, 1510, 1223, 985, 887, 831, 814 cm$^{-1}$

EXAMPLE 14

Preparation of trans-4-(2-(p-fluorophenyl)ethyl)-1-n-pentyl-1-silacyclohexane

Hydrogen chloride gas was blown into a solution, in 200 ml of benzene, of 36.0 g of trans-4-(2-(p-fluorophenyl)ethyl)-1,1-diphenyl-1-silacyclohexane and 5.0 g of aluminium chloride to obtain 30.0 g of trans-4-(2-(p-fluorophenyl)ethyl)-1,1-dichloro-1-silacyclohexane. The product was dissolved in 100 ml of THF, which was added to a solution of 1.0 g of lithium aluminium hydride serving as a reducing agent in 100 ml of THF at 0° C. The reaction mixture was agitated as it is for 30 minutes, followed by removal of the reducing agent and concentration of the resultant filtrate to obtain 4-(2-(p-fluorophenyl)ethyl)-1-chloro-1-silacyclohexane. This product was dissolved in 50 ml of THF and dropped in 100 ml of a THF solution of 1 mole/liter of n-pentylmagnesium bromide at room temperature, followed by extraction with ethyl acetate. The ethyl acetate solution was washed with brine, dried and concentrated by a usual manner, followed by purification through silica gel chromatography to obtain 26.8 g of the intended product. The results of IR analysis are shown below.

IR (liquid film) $v_{max}$: 2918, 2852, 2098, 1601, 1510, 1223, 887, 823 cm$^{-1}$

EXAMPLE 15

Preparation of trans, trans-2-fluoro-4-(4-n-pentyl-4-silacyclohexyl)-4'-(4-n-propylhexyl)biphenyl The general procedure of Example 1 was repeated using 2-fluoro-4-(4,4-diphenyl-4-silacyclohexyl)-4'-(trans-4-n-propylcyclohexyl)biphenyl and a THF solution of n-pentylmagnesium bromide, thereby obtaining the intended compound. The results of measurement of liquid crystal temperature ranges and IR analysis are shown below.

Liquid crystal temperature range: C79.0S95.0N247.0I (i.e. C-N transition temperature of 79.0° C., S-N transition temperature of 95.0° C. and N-I transition temperature of 247.0° C.)

IR (KBr, disc) $v_{max}$: 2920, 2848, 2098, 1493, 1404, 1194, 987, 887, 812 cm$^{-1}$

EXAMPLE 16

Preparation of trans, trans-4-(4-methoxycylohexyl)-1-n-propyl-1-silacyclohexane

The general procedure of Example 1 was repeated using 4-(trans-4-methoxycyclohexyl)-1,1-diphenyl-1-silacyclohexane and a THF solution of n-propylmagnesium bromide, thereby obtaining the intended compound. The results of measurement of liquid crystal temperature ranges and IR analysis are shown below.

Liquid crystal temperature range: C<−60N−40.0I (i.e. C-N transition temperature of lower than −60° C, and N-I transition temperature of −40.0° C.)

IR (liquid film) $v_{max}$: 2928, 2856, 2820, 2098, 1452, 1103, 989, 887, 843, 820 cm$^{-1}$

EXAMPLE 17

Preparation of 4-(2-(trans-4-n-pentyl-4-silacyclohexyl)ethyl)-3',4'-difluorobiphenyl The general procedure of Example 1 was repeated using 4-(2-(4,4-diphenyl-4-silacyclohexyl)ethyl)-3',4'-difluorobiphenyl and a THF solution of n-pentylmagnesium bromide, thereby obtaining the intended compound. The results of measurement of liquid crystal temperature ranges and IR analysis are shown below. Liquid crystal temperature range: C38.6N58.2I (i.e. C-N transition temperature of 38.6° C., and N-I transition temperature of 58.2° C.)

IR (liquid film) $v_{max}$: 2920, 2850, 2100, 1605, 1504, 1311, 1267, 814 cm$^{-1}$

EXAMPLE 18

Preparation of trans, trans-4-(4-(4-n-propyl-4-silacyclohexyl)cyclohexyl)-3',4'-difluorobiphenyl The general procedure of Example 1 was repeated using 4-(trans-4-(4,4-diphenyl-4-silacyclohexyl)cyclohexyl)-3',4'-difluorobiphenyl and a THF solution of n-propylmagnesium bromide, thereby obtaining the intended compound.

The results of measurement of liquid crystal temperature ranges and IR analysis are shown below.

Liquid crystal temperature range: C82.7S107.5N229.1I (i.e. C-S transition temperature of 82.7° C., S-N transition temperature of 107.5° C. and N-I transition temperature of 229.1° C.)

IR (KBr, disc) $v_{max}$: 2916, 2848, 2104, 1533, 1506, 1279, 985, 889, 845, 814 cm$^{-1}$

EXAMPLE 19

Preparation of 4-(trans-4-n-pentyl-4-silacyclohexyl)-2,4''-difluoroterphenyl

The general procedure of Example 1 was repeated using 4-(4,4-diphenyl- 4-silacyclohexyl)-2,4''-difluoroterphenyl and a THF solution of n-pentylmagnesium bromide, thereby obtaining the intended compound. The results of measurement of liquid crystal temperature ranges and IR analysis are shown below.

Liquid crystal temperature range: C87.8S135.0N250.3I (i.e. C-S transition temperature of 87.8° C., S-N transition temperature of 135.0° C. and N-I transition temperature of 250.3° C.)

IR (KBr, disc) $v_{max}$: 2918, 2846, 2106, 1487, 1223, 887, 816 cm−1

EXAMPLE 20

Preparation of trans-4-(4-n-pentyl-4-silacyclohexyl)-2-fluoro-4 '-(2-(3,4-difluorophenyl)ethyl)biphenyl The general procedure of Example 1 was repeated using 4-( 4,4-diphenyl-4-silacyclohexyl)-2-fluoro-4 '-(2-(3,4-difluorophenyl)ethyl)biphenyl and a THF solution of n-pentylmagnesium bromide, thereby obtaining the intended compound. The results of measurement of liquid crystal temperature ranges and IR analysis are shown below.

Liquid crystal temperature range: C49.5(SA)50.6N150.5I (i.e. C-(SA) transition temperature of 49.5° C., (SA)-N transition temperature of 50.6° C. and N-I transition temperature of 150.5° C.)

IR (KBr, disc) $v_{max}$: 2920, 2102, 1518, 1491, 1404, 1290, 1286, 1120, 889, 818 cm−1

EXAMPLE 21

Preparation of trans, trans-4-(2-(4-(4-n-propyl- 4-silacyclohexyl)cyclohexyl)ethyl)-4'-chloro-3'-fluorobiphenyl The general procedure of Example 1 was repeated using 4-2-(trans-4-( 4,4-diphenyl-4-silacyclohexyl)cyclohexyl)ethyl)-4'-chloro-3'-fluorobiphenyl a THF solution of n-propylmagnesium bromide, thereby obtaining the intended compound. The results of measurement of liquid crystal temperature ranges and IR analysis are shown below.

Liquid crystal temperature range: C63.3N208.0I (i.e. C-N transition temperature of 63.3° C. and N-I transition temperature of 208.0° C.)

IR (KBr, disc) $v_{max}$: 2920, 2850, 2096, 1560, 1481, 1200, 1070, 982, 889, 845, 805 cm$^{-1}$ As will be apparent from the foregoing description, trans isomers of silacyclohexane compounds having a silicon atom in the molecule can be selectively prepared, according to the invention, as exhibiting liquid crystal properties. The thus prepared silacyclohexane liquid crystal compounds are very useful as a material for liquid crystal displays. Additionally, when Si-containing liquid crystal compounds are prepared according to the process of the invention, the length and type of folded chain can be determined at a final step of a multi-stage procedure. In the field of applications of liquid crystals wherein a number of liquid crystal compounds have to be prepared to form a liquid crystal composition, it will not be possible to prepare such a liquid crystal composition making use of Si-free liquid crystal compounds alone. According to the invention, a diversity of Si-containing liquid crystal compounds can be efficiently, economically prepared.

What is claimed is:

1. A process for preparing a silacyclohexane compound, which comprises the steps of:

(1) subjecting a diarylsilacyclohexane compound of the following general formula

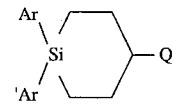

wherein Ar and Ar' independently represent a phenyl group or a tolyl group, and Q represents a group of the following general formula

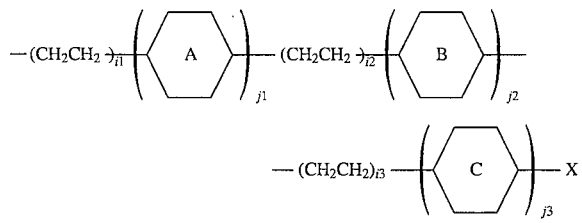

in which

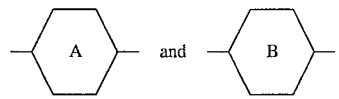

independently represent

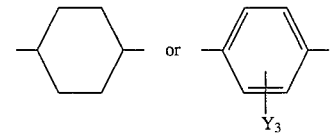

wherein $Y_3$ represents H, F or CH$_3$;

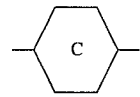

represents

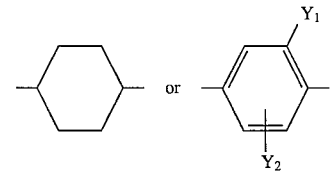

wherein $Y_1$ and $Y_2$ independently represent H, F or Cl;
X represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, CF$_3$, CF$_2$Cl, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and i1, i2 and i3 are, respectively, 0 or 1 provided that i1+i2+i3=1 and j1, j2 and j3 are, respectively, a value of 0, 1 or 2 provided that j1+j2+j3=0, 1 or 2, to conversion into a dihalosilacyclohexane compound of the following general formula

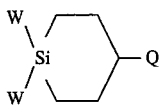

wherein each W represents a halogen;

(2) subjecting the resultant dihalosilacyclohexane compound to further reaction with an alcohol of the general formula, R'OH, wherein R' represents a linear alkyl group having from 1 to 10 carbon atoms or a branched alkyl group having from 3 to 8 carbon atoms, thereby obtaining a dialkoxysilacyclohexane compound of the following general formula

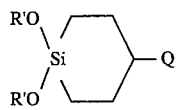

(3) reducing the dialkoxysilacyclohexane compound to obtain a dihydrosilacyclohexane compound of the following general formula

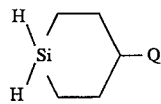

(4) subjecting the dihydrosilacyclohexane compound to monohalogenation to obtain a hydrohalosilacyclohexane compound of the following general formula

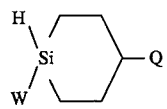

wherein W represents a halogen; and (5) subjecting the hydrohalosilacyclohexane compound to reaction with an organometallic reagent of the general formula, Q'—M, wherein (a) Q' represents a group of the following general formula

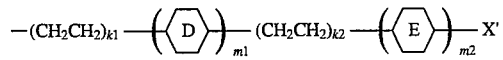

in which

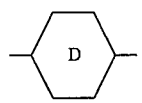

represents

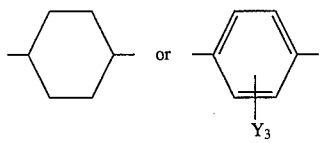

wherein $Y_3$ represents H, F or $CH_3$;

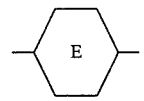

represents

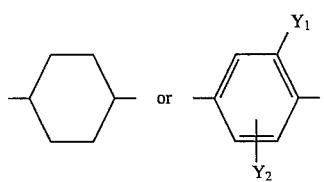

wherein $Y_1$ and $Y_2$ independently represent H, F or Cl; X' represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and k1 and k2 are independently a value of 0 or 1 provided that k1+k2=1, m1 and m2 are independently represent a value of 0, 1 or 2 provided that m1+m2=0, 1 or 2; and (b) M represents MgP or ZnP wherein P represents a halogen, thereby obtaining a silacyclohexane compound of the following general formula

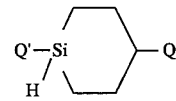

wherein Q' and Q have, respectively, the same meanings defined above.

2. A process according to claim 1, wherein in step (1), the diarylsilacyclohexane compound is converted to the dihalosilacyclohexane compound by reaction with an electrophilic reagent.

3. A process according to claim 1, wherein the conversion of the step (1) is effected by addition of a Lewis acid or by irradiation of actinic light.

4. A process according to claim 3, wherein said Lewis acid is solid and is removed prior to the step (5).

5. A process according to claim 1, wherein the alcohol used in the step (2) is a lower alcohol.

6. A process for preparing a silacyclohexane compound comprising the steps of:

(1) subjecting a diarylsilacyclohexane compound of the following general formula

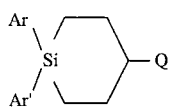

wherein Ar and Ar' independently represent a phenyl group or a tolyl group, and Q represents a group of the following formula

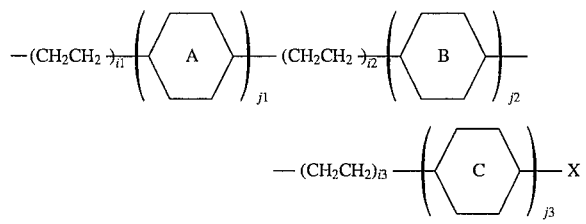

in which

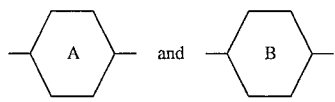

independently represent

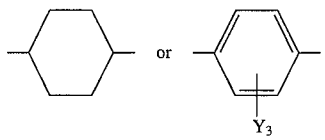

wherein $Y_3$ represents H, F or $CH_3$;

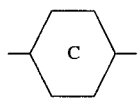

represents

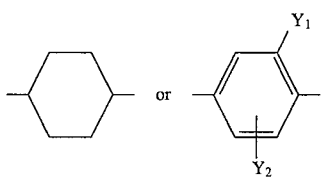

wherein $Y_1$ and $Y_2$ independently represent H, F or Cl; X represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and i1, i2 and i3 are, respectively, a value of 0 or 1 provided that i1+i2+i3=1 and j1, j2 and j3 are, respectively, a value of 0, 1 or 2 provided that j1+j2+j3=0, 1 or 2, to conversion into a dihalosilacyclohexane compound of the following general formula

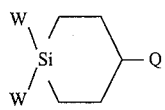

wherein each W represents a halogen;

(2) reducing the dihalosilacyclohexane compound to obtain a dihydrosilacyclohexane compound of the following general formula

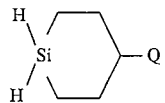

(3) subjecting the dihydrosilacyclohexane compound to monohalogenation to obtain a hydrohalosilacyclohexane compound of the following general formula

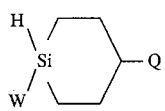

wherein W represents a halogen; and (4) subjecting the hydrohalosilacyclohexane compound to reaction with an organometallic reagent of the general formula, Q'—M, wherein (a) Q' represents a group of the following formula

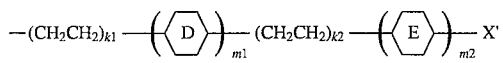

in which

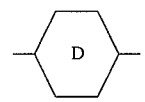

represents

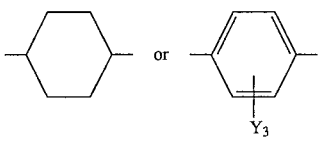

wherein $Y_3$ represents H, F or $CH_3$;

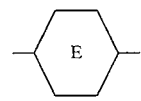

represents

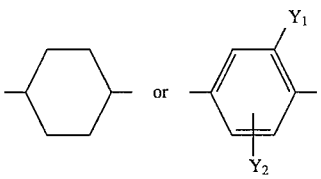

wherein $Y_1$ and $Y_2$ independently represent H, F or Cl; X' represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and k1 and k2 are independently a value of 0 or 1 provided that k1+k2=1, m1 and m2 are independently represent a value of 0, 1 or 2 provided that m1+m2=0, 1 or 2; and (b) M represents MgP or ZnP wherein P represents a halogen, thereby obtaining a silacyclohexane compound of the following general formula

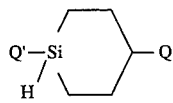

wherein Q' and Q have, respectively, the same meanings defined above.

7. A process according to claim 6, wherein in step (1), the diarylsilacyclohexane compound is converted to the dihalosilacyclohexane compound by reaction with an electrophilic reagent.

8. A process according to claim 6, wherein the conversion of the step (1) is effected by addition of a Lewis acid or by irradiation of actinic light.

9. A process for preparing a silacyclohexane compound comprising the steps of:

(1) subjecting a diarylsilacyclohexane compound of the following general formula

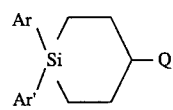

wherein Ar and Ar' independently represent a phenyl group or a tolyl group, and Q represents a group of the following general formula

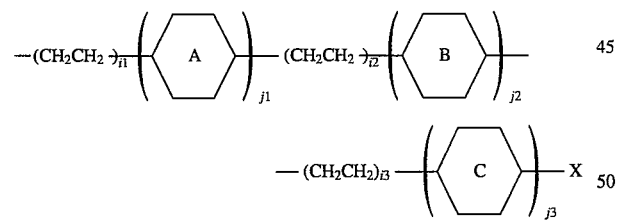

in which

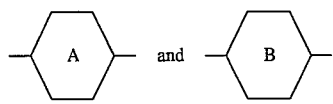

independently represent

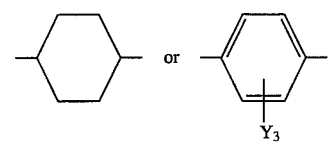

wherein $Y_3$ represents H, F or $CH_3$;

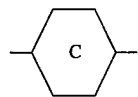

represents

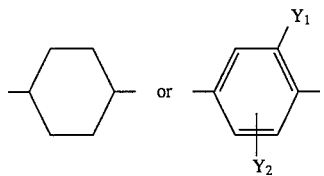

wherein $Y_1$ and $Y_2$ independently represent H, F or Cl;

X represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and i1, i2 and i3 are, respectively, a value of 0 or 1 provided that i1+i2+i3=1 and j1, j2 and j3 are, respectively, a value of 0, 1 or 2 provided that j1+j2+j3=0, 1 or 2, to conversion into a dihalosilacyclohexane compound of the following general formula

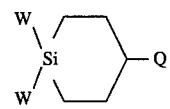

wherein each W represents a halogen;

(2) reducing the dihalosilacyclohexane compound under conditions sufficient to obtain a hydrohalosilacyclohexane compound of the following general formula

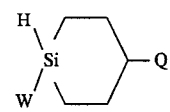

wherein W has the same meaning as defined above; and (3) subjecting the hydrohalosilacyclohexane compound to reaction with an organometallic reagent of the general formula, Q'—M, wherein (a) Q' represents a group of the following general formula

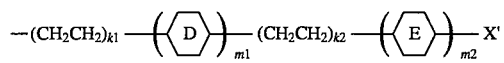

in which

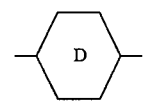

represents

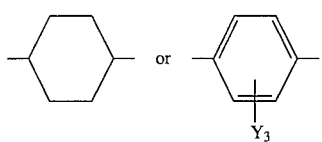

wherein Y₃ represents H, F or CH₃;

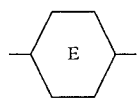

represents

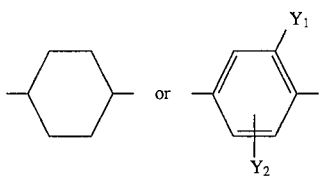

wherein $Y_1$ and $Y_2$ independently represent H, F or Cl; X' represents R or OR, in which each R represents a linear alkyl group having from 1 to 10 carbon atoms, a branched alkyl group having from 3 to 8 carbon atoms, an alkoxyalkyl group having from 2 to 7 carbon atoms or an alkenyl group having from 2 to 8 carbon atoms, CN, F, Cl, $CF_3$, $CF_2Cl$, $OCF_3$, $OCHF_2$, $OCF_2Cl$, $OCHFCl$, $(O)_mCT=CX_1X_2$, or $O(CH_2)_r(CF_2)_sX_3$ wherein m is a value of 0 or 1, T and $X_1$ independently represent H, F or Cl, $X_2$ represents F or Cl, r and s are, respectively, a value of 0, 1 or 2 provided that r+s=2, 3 or 4, and $X_3$ represents F or Cl; and k1 and k2 are independently a value of 0 or 1 provided that k1+k2=1, m1 and m2 are independently represent a value of 0, 1 or 2 provided that m1+m2=0, 1 or 2; and (b) M represents MgP or ZnP wherein P represents a halogen, thereby obtaining a silacyclohexane compound of the following general formula

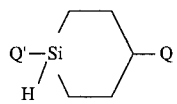

wherein Q' and Q have, respectively, the same meanings defined above.

10. A process according to claim 9, wherein in step (1), the diarylsilacyclohexane compound is converted to the dihalosilacyclohexane compound by reaction with an electrophilic reagent.

11. A process according to claim 9, wherein the conversion of the step (1) is effected by addition of a Lewis acid or by irradiation of actinic light.

* * * * *